: US005360317A

United States Patent [19]
Clausen et al.

[11] Patent Number: 5,360,317
[45] Date of Patent: Nov. 1, 1994

[54] CENTRIFUGAL BLOOD PUMP

[75] Inventors: Earl W. Clausen, Eden Prairie; Lloyd C. Hubbard, Excelsior, both of Minn.

[73] Assignee: Spin Corporation, Excelsior, Minn.

[21] Appl. No.: 163,393

[22] Filed: Dec. 6, 1993

Related U.S. Application Data

[63] Continuation of Ser. No. 922,198, Jul. 30, 1992, abandoned.

[51] Int. Cl.⁵ .............................................. F04D 29/04
[52] U.S. Cl. ..................................... 415/206; 415/900
[58] Field of Search ................. 415/203, 206, 900; 417/423.12, 424.1, 424.2, 420

[56] References Cited

U.S. PATENT DOCUMENTS

| | | | |
|---|---|---|---|
| 3,957,389 | 5/1976 | Rafferty et al. | 415/900 |
| 4,036,584 | 7/1977 | Glass | 415/203 |
| 4,507,048 | 3/1985 | Belenger et al. | 415/900 |
| 4,589,822 | 5/1986 | Clausen et al. | 415/170 |
| 4,606,698 | 8/1986 | Clausen et al. | 415/170 |
| 4,643,641 | 2/1987 | Clausen et al. | 415/900 |
| 4,854,820 | 8/1989 | Zolotar et al. | 415/171.1 |
| 4,898,518 | 2/1990 | Hubbard et al. | 415/900 |
| 4,984,972 | 1/1991 | Clausen et al. | 417/420 |
| 5,017,103 | 5/1991 | Dahl | 417/420 |
| 5,147,187 | 9/1992 | Ito et al. | 415/900 |
| 5,195,877 | 3/1993 | Kletschka | 415/900 |

Primary Examiner—John T. Kwon
Attorney, Agent, or Firm—Kinney & Lange

[57] ABSTRACT

A centrifugal pump for pumping biological fluids such as blood includes a housing which defines a pumping chamber. The pumping chamber encloses an impeller mounted on a spindle. The impeller carries coupling mechanisms which couple with an external source of rotation to rotate the impeller. The spindle allows the impeller to rotate freely, but both ends of the spindle are constrained in the axial and lateral directions. The housing includes an inlet and an outlet.

12 Claims, 4 Drawing Sheets

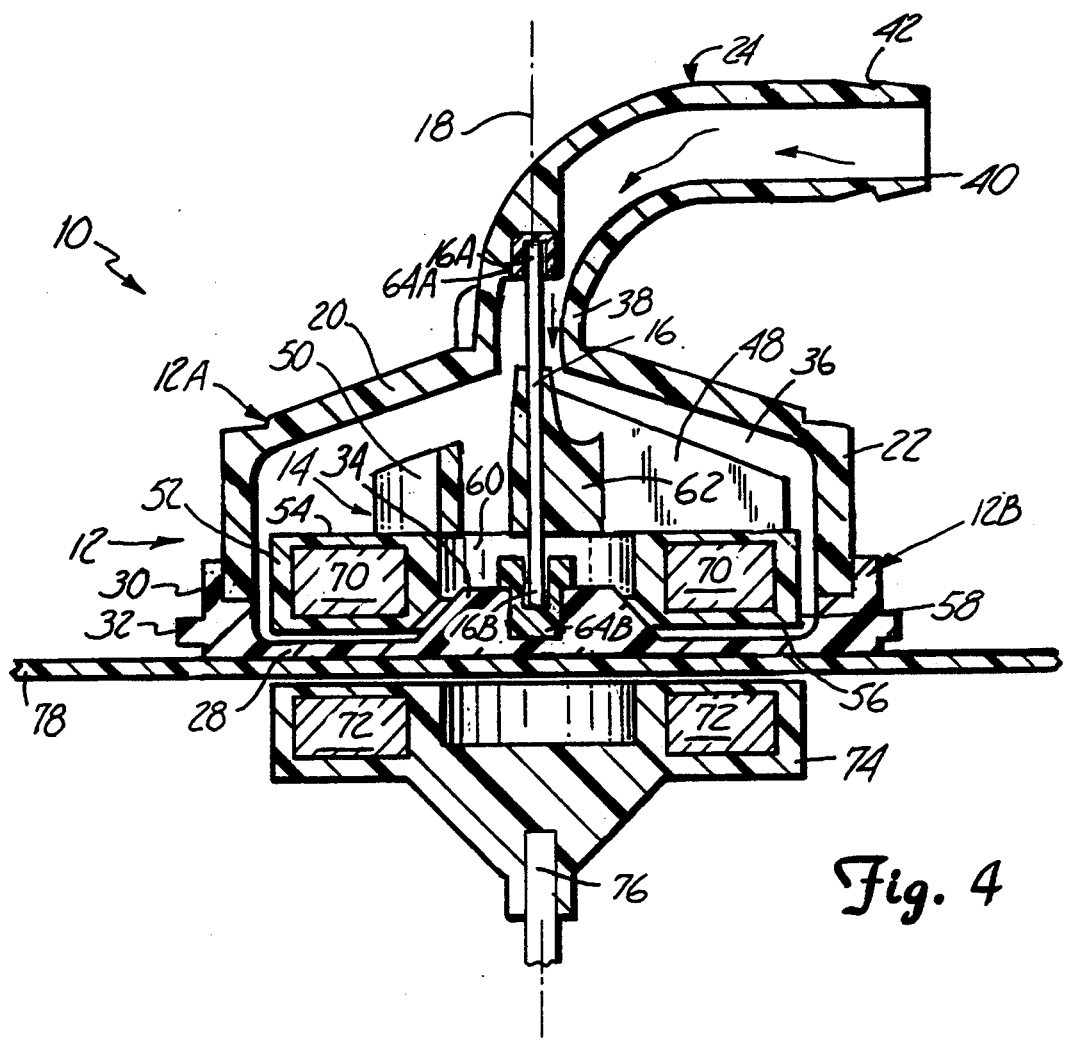
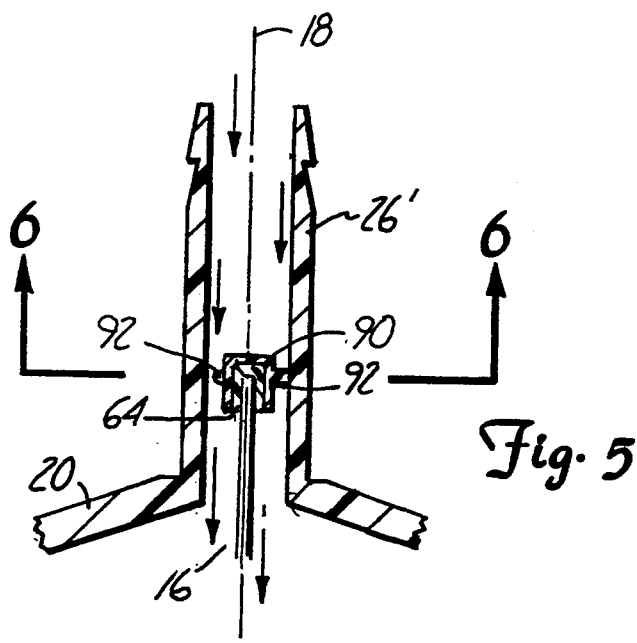
Fig. 4
Fig. 5
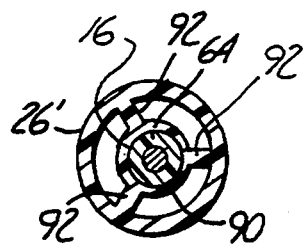
Fig. 6

CENTRIFUGAL BLOOD PUMP

This is a continuation of application Ser. No. 07/922,198, filed Jul. 30, 1992, now abandoned.

BACKGROUND OF THE INVENTION

The present invention relates to pumps and more particularly to centrifugal blood pumps without the requirement of a rotating seal to protect the pump bearings from the pumped blood.

Delicate surgical procedures require that the site of surgery remain motionless during the surgical process. This made early heart surgery difficult to impossible as interruption of the heart's pumping action for the required length of time would be invariably fatal.

During the 1960s, prolonged and non-fatal stoppage of the heart became possible by use of newly developed "heart-lung" machines. These machines consisted of a mechanical blood pump combined with a blood oxygenator. They were capable of taking over the function of the natural heart and lungs for periods of up to several hours, enabling the development of techniques leading to today's extensive practice of open-heart surgery.

The first practical mechanical blood pumps used were peristaltic or "roller" pumps. The pumping action of a roller pump derives from the compression of a section of the flexible plastic tubing which carries the blood through the heart-lung machine. A moving roller presses the tubing against a semicircular platen, moving the blood forward in the tubing. The speed of the moving roller and the diameter of the tubing control the rate of blood flow.

Although the roller pump was and is simple and reliable, it has two characteristics which can endanger the patient undergoing surgery. First, if flow is inadvertently obstructed, the pressure produced by a roller pump may exceed the bursting strength of the tubing circuit. Second, if air is accidentally introduced into the tubing circuit, it will be pumped to the patient along with the blood. Either of these conditions may result in serious or fatal consequences to the patient.

In 1976, centrifugal blood pumps began to replace the roller pump as the "heart" of the heart-lung machine. The pumping action of a centrifugal pump derives from the rotation of an impeller within a pumping chamber. Pump pressure is controlled by the rotational speed of the impeller. At operational speeds, excessive pressure cannot be produced. Additionally, the centrifugal forces in the pump form a natural air trap and, with massive introduction of air, deprime and discontinue pumping altogether. These two safety features, and the lower blood damage caused by these pumps, is now widely recognized, and has led to their extensive use for open heart surgery.

In the early 1980s it was demonstrated that a mechanical blood pump could be used as a heart-assist pump for patients who could not be separated from the heart-lung machine following surgery. The readily available centrifugal blood pumps were quickly applied to this situation as well as to the more routine use during heart surgery.

The fragility of the blood presents several problems for the design of mechanical blood pumps. Excessive shear forces cause rupture of the red blood cells (hemolysis). High flow velocity rates are needed over local areas of friction (such as seals) to prevent points of high temperature which cause blood damage and the accumulation of clot deposits.

Application of rotational impeller motion by conventional shaft drives has not been practical due to the need for a sterile barrier between the pumped blood and the pump drive mechanism. For this reason, centrifugal blood pumps commonly utilize a magnetic coupling between the pump impeller (or impeller shaft) and the drive motor.

Previous centrifugal blood pumps have relied on conventional ball bearings to support the impeller shaft. A rotating seal was used to protect the bearings from contamination by the pumped blood. Some centrifugal blood pumps utilized magnets carried by the impeller, which was supported by bearings mounted on a stationary shaft. A shaft seal was also required to protect the bearings from contamination by the pumped blood.

Due to the corrosive nature of blood, shaft seals usually fail after a relatively short time, exposing the bearings to contamination. If the failure is not detected, bearings may overheat, causing damage to the blood. Blood damage can lead to hemolysis, clot formation and stroke. The short useful life of current centrifugal blood pumps mandates their frequent replacement and is the single most important problem yet to be solved with these devices.

SUMMARY OF THE INVENTION

The present invention is a sealless centrifugal pump for pumping biological fluids such as blood. The pump has a housing which defines a pumping chamber. An impeller which rotates about an axis is disposed within the pumping chamber. The pumping chamber has an inlet provided at the impeller axis of rotation and an outlet provided along the periphery of the impeller. An external source of rotation is disposed outside the pumping chamber which causes the impeller to rotate. The housing has constraining mechanisms (preferably journal bearings) which constrain both the inlet side and the base side of the impeller from movement in both axial and lateral directions.

Because there are no moving parts which extend through a wall of the housing, and particularly because there is no torque-providing shaft which extends through a housing wall, the present invention has no seal around a moving part and no opportunity for seal failure. Because the source of rotation does not contact the blood, sterility can be ensured. Because the impeller is constrained both on its inlet and base side from movement in both the axial and lateral directions, there is no opportunity for dislocation or misalignment of the impeller.

BRIEF DESCRIPTION OF THE DRAWINGS

FIG. 4 is a cross-sectional side view of the present invention as seen from section line 4—4 of FIG. 2.

FIG. 5 is an cross-sectional side view of an alternate embodiment of the inlet bearing surface of the present invention.

FIG. 6 is a cross-sectional top view of the alternate embodiment of the inlet bearing surface as seen from section line 6—6 of FIG. 5.

DETAILED DESCRIPTION OF THE PREFERRED EMBODIMENTS

A First Embodiment—FIGS. 1-4

Figure 1:
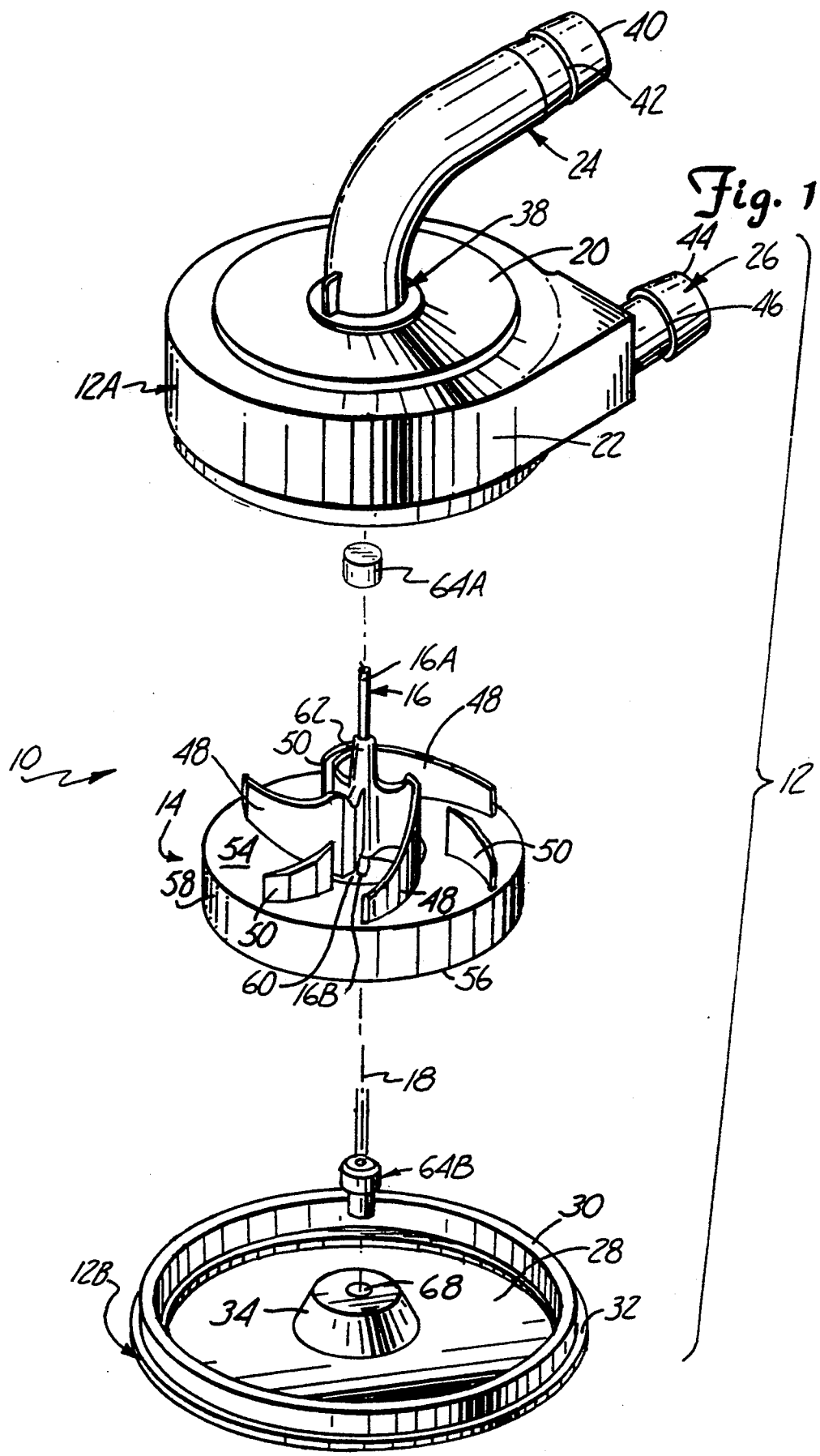
FIG. 1 is an exploded perspective view of the present invention.
Figure 2:
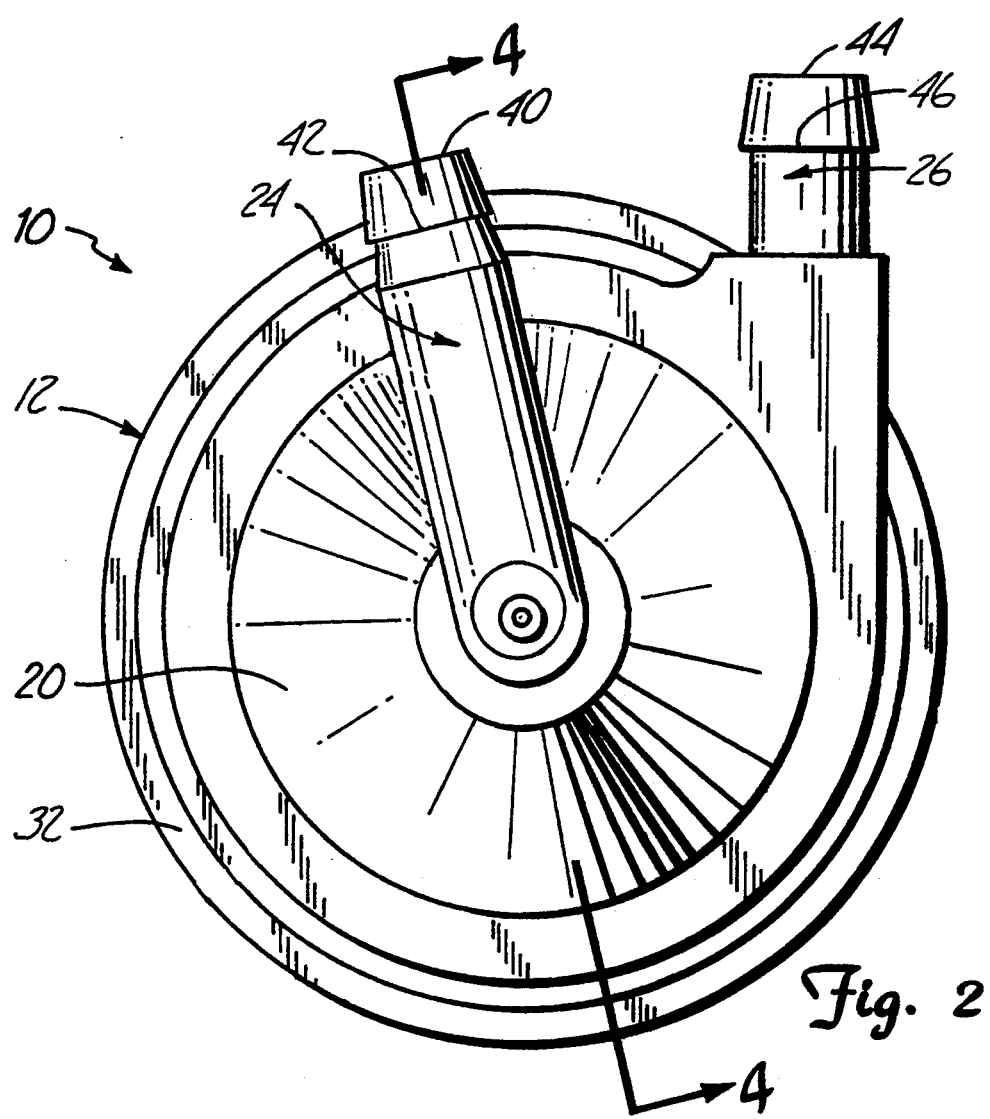
FIG. 2 is a top plan view of the present invention.

A preferred embodiment of a centrifugal blood pump 10 of the present invention is shown in FIGS. 1-4. Blood pump 10 includes housing 12 which encloses impeller 14 and support shaft or spindle 16. Impeller 14 and spindle 16 rotate about axis of rotation 18. Housing 12 has separate parts for ease of assembly, including upper enclosure 12A and base 12B, which are connected and sealed together, such as by ultrasonic welding.

Upper enclosure 12A includes inlet wall 20, circumferential wall 22, inlet 24, and outlet 26. Base 12B includes bottom wall 28, cylindrical side wall 30, mounting flange 32, and pedestal 34. Pumping chamber 36 (FIG. 4) is defined as the volume enclosed by inlet wall 20, circumferential wall 22 and bottom wall 28.

Inlet 24 is a J-shaped tubular member which has one end 38 attached to inlet wall 20 and an opposite free end 40. Ridge 42 on an outer surface of inlet 24 facilitates attachment of inlet tubing (not shown) from a reservoir/oxygenator or from the patient to free end 40 of inlet 24.

Outlet 26 is a tubular member which extends from circumferential wall 22 to free end 44. Ridge 46, adjacent free end 44, facilitates attachment to outlet 26 of outlet tubing (not shown) which leads to the patient.

Figure 3A:
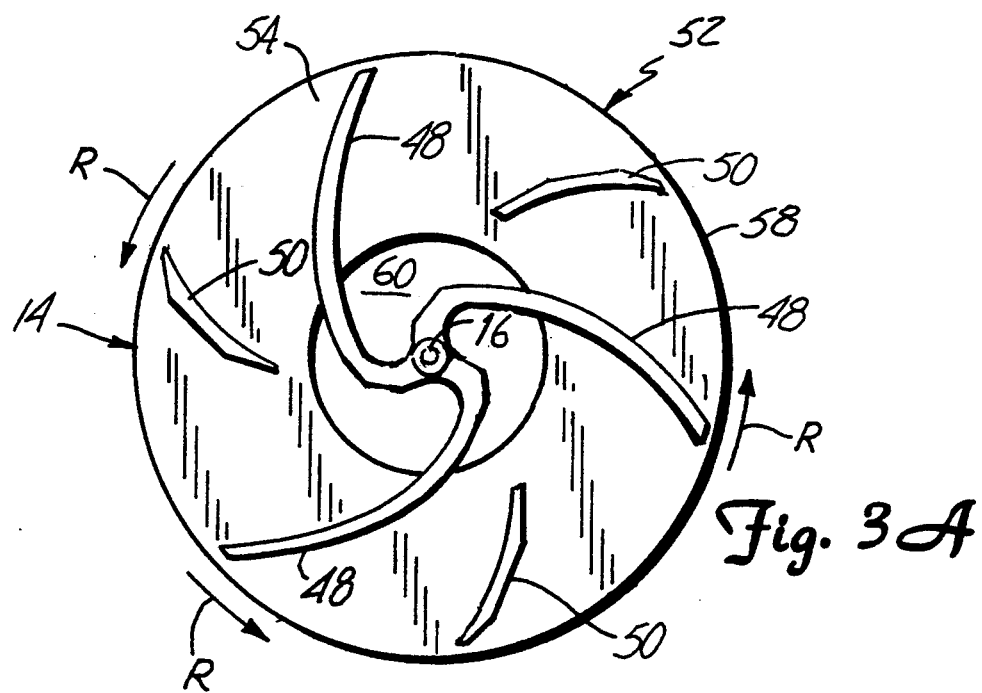
FIGS. 3A and 3B are top and bottom plan views of the impeller of the present invention.

As shown in FIG. 3A, impeller 14 rotates about axis of rotation 18 with a direction of rotation indicated by arrow R. Impeller 14 has full impeller blades 48 and short impeller blades 50 which are attached to platform section 52 of impeller 14. Platform section 52 is disk-shaped and includes top surface 54, bottom surface 56, outer cylindrical surface 58 and central circulation hole 60. Full blades 48 extend from hub 62 across central circulation hole 60 to platform section 52, while short blades 50 extend only along top surface 54 of platform section 52.

Figure 3B:
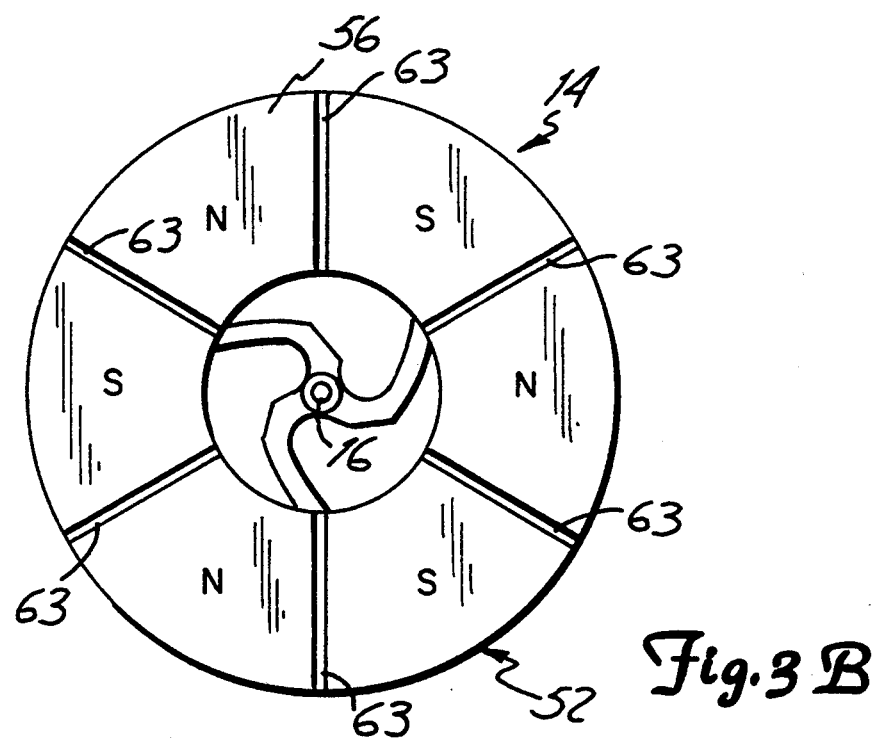

As shown in FIG. 3B, bottom surface 56 of platform section 52 contains a plurality of radial grooves 63. The purpose of grooves 63 is to counteract a tendency of impeller 14 to shift in the axial direction toward inlet 24 as impeller 14 rotates.

FIG. 4 shows impeller 14 attached to spindle 16, so that impeller 14 and spindle 16 rotate together about axis of rotation 18. Inlet end 16A of spindle 16 extends into and rotates within journal bearing 64A. Base end 16B of spindle 16 extends into and rotates within journal bearing 64B.

The constraining mechanism of the present invention is provided by journal bearings 64A and 64B, which capture and support spindle 16 while permitting spindle 16 to rotate. Journal bearings 64A,64B are disposed coaxially with and circumferentially around axis of rotation 18. Journal bearing 64A is press fit into recess 66 in the interior side wall of inlet 24. Journal bearing 64B is press fit into recess 68 in pedestal 34.

The inner diameters of the recesses of journal bearings 64A and 64B are slightly greater than the outer diameters of the respective ends 16A,16B of spindle 16, so that a small lateral clearance is defined. The distance between the inner end surfaces of journal bearings 64A,64B is slightly greater than the length of spindle 16, defining a small axial clearance.

Platform section 52 of impeller 14 contains magnets 70, which couple with magnets 72 carried by rotor 74, to rotate impeller 14 and spindle 16 about axis of rotation 18. Electric motor drive shaft 76 is connected to rotor 74 and provides torque to rotate magnets 72 and rotor 74 about axis of rotation 18. Magnets 70 and 72 couple together so that impeller 14 rotates at the same speed as rotor 74. The speed of drive shaft 76, therefore, determines the speed of impeller 14.

Impeller 14 is attached to spindle 16 such that bottom surface 56 of platform section 52 is a small distance above bottom wall 28. Impeller 14 fits within pumping chamber 36 to leave clearance between the top and sides of impeller 14 and upper enclosure member 12A.

Housing 12 is shown in FIG. 4 adjacent thin mounting surface 78. Housing 12 includes mounting flange 32, which may facilitate attachment of the housing 12 to the mounting surface 78. Housing 12 may be attached to the mounting surface 78 by an attachment mechanism (not shown) so as to provide correct positioning of the blood pump 10 with respect to the external source of rotation (i.e., rotor 74 and magnets 72).

Operation of the First Embodiment

Blood from the patient enters pumping chamber 36 through inlet 24. As it enters pumping chamber 36, inlet flow is in the axial direction at axis of rotation 18. This orientation and location of inlet flow allows the blood to make a gentle directional transition without placing excess forces on the blood. The blood contacts rotating impeller blades 48 and 50, and is propelled to and through outlet 26 and back to the patient.

Blood pump 10 of the present invention is magnetically driven by a source of rotation which is external to pumping chamber 36. Therefore, blood pump 10 of the present invention does not have a torque-providing shaft or other part extending through a wall of housing 12. This eliminates the need for a seal and the possibility of seal wear and leakage.

The possibility of dislocation or misalignment of impeller 14 is prevented by spindle 16 being constrained in the axial and the lateral directions by journal bearings 64A and 64B. Bottom surface 56 of impeller 14 does not contact bottom wall 28, preventing any friction between these surfaces. The clearance between the top and sides of impeller 14 and enclosure 12A likewise prevents any friction between these surfaces.

The structure of the constraining mechanism reduces the amount of friction between the rotating spindle 16 and the housing 12. The small lateral clearance between the ends 16A,16B of spindle 16 and journal bearings 64A,64B allows for slight lateral movement of spindle 16 and ensures minimal pressure between parts. This allows minimal friction and minimal heat buildup between ends 16A,16B of spindle 16 and journal bearings 64A,64B. The small axial clearance between ends 16A,16B of the spindle 16 and the inner end surfaces of journal bearings 64A,64B ensures minimal pressure between parts, again reducing friction and heat buildup.

Bearings 64A,64B of the present invention are located in areas of high blood flow velocity. Base journal bearing 64B is located by pedestal 34 in the center of central circulation hole 60. Inlet journal bearing 64A is located in inlet 24, and is exposed to the inlet flow of blood into pumping chamber 36. The location of bearings 64A,64B ensures rapid dissipation of any frictional heat that is created.

Mounting flange 32 allows blood pump 10 to be quickly and easily removed, and a new pump can be quickly and easily attached. Quick and easy removal and attachment of the pump is useful for the frequent replacement necessary to ensure sterility. Quick replacement also aids in the event of a pump malfunction. Because the source of rotation does not have to be replaced with replacement of the rest of the pump, the cost of replacement is lowered.

An important feature of blood pump 10 is the elimination of the requirement for a shaft seal. It was described previously that early failure of the shaft seal is the primary reason for the relatively short operational life of currently available centrifugal blood pumps.

Elimination of the shaft seal requires that bearings be designed which can operate effectively in blood. By using spindle 16 with a minimum diameter consistent with the required shaft strength, surface velocity is minimized. Minimization of surface velocity also minimizes friction, frictional heat and shear forces, all of which can cause blood damage and clot formation.

While a small diameter for spindle 16 is beneficial in reducing blood damage, it also reduces the areas of spindle 16 which serve as axial thrust bearings, namely at both ends 16A and 16B of spindle 16. Since pump 10 is driven by magnetic coupling, there is an axial load in the direction of the magnetic coupling (i.e., toward rotor 74) when pump 10 is at rest or operating at low speeds. The use of a magnetic coupling requires a close proximity of impeller magnet 70 and drive magnet 72. Therefore, the preferred design is to have impeller blades 48 and 50 only on the side of impeller 14 which faces the pump inlet 24. This causes an asymmetrical axial flow across the two faces of impeller 14 and results in an increasing axial force toward pump inlet 24 as flow increases (the "lifting force"). The required area of the axial thrust bearing and hence, the minimum diameter of is spindle 16 determined by this maximum axial load.

As shown in FIG. 3B, the lifting force is preferably counteracted by placing radial grooves 63 in the base side of impeller 14 to increase the axial flow across this surface. The use of grooves 63, rather than blades, does not require increased space between the driven and drive magnets 70 and 72 (which would require more or stronger magnets to maintain the same coupling strength). By proper selection of the number and depth of grooves 63, pump 10 can be designed such that the lifting force "floats" impeller 14 such that, within the operating rpm of pump 10, the axial load on both bearings 64A and 64B and both spindle ends 16A and 16B is minimal. This reduces frictional heat, blood damage and bearing wear.

In a preferred embodiment, a groove 63 extends radially between adjacent magnets 70 of opposite polarity. This is illustrated in FIG. 3B by the polarity symbols "N" and "S".

A Second Embodiment—FIGS. 5–6

An alternative embodiment of the present invention is shown in FIGS. 5 and 6. This embodiment has journal bearing 64A disposed in the center of straight inlet tube 26'. Journal bearing 64A is supported in cup 90 by struts 92, which extend from cup 90 to the inner wall of inlet 26'. This allows inlet 26' to remain straight (rather than J-shaped as in FIG. 1) while still providing inlet flow in the axial direction at axis of rotation 18.

Although the present invention has been described with reference to preferred embodiments, workers skilled in the art will recognize that changes may be made in form and detail without departing from the spirit and scope of the invention. For instance, a stationary pin going through a central hole in hub 62 of impeller 14 may be substituted for spindle 16, such that the top side and the bottom side of impeller 14 are constrained from movement in the axial and lateral directions by the stationary pin, while impeller 14 remains free to rotate around the pin. Also, in some embodiments grooves 63 are not required and therefore are omitted.

What is claimed is:

1. A centrifugal pump for pumping biological fluids such as blood, adapted to be coupled with an external source of rotation, comprising:
   a housing defining a pumping chamber with an inlet and an outlet;
   a spindle enclosed within the pumping chamber for rotation about a spindle axis of rotation, the spindle comprising an inlet end toward the inlet of the pumping chamber and a base end opposite the inlet end;
   an impeller enclosed within the pumping chamber and being supported on the spindle in a spaced relationship to the external source of rotation, the impeller comprising coupling means for coupling with the external source of rotation for rotating the impeller about the spindle axis of rotation;
   an inlet journal bearing for rotatably supporting and receiving the inlet end of the spindle, the inlet journal bearing having a cylindrical inner side wall and an inner end surface;
   a base journal bearing for rotatably supporting and receiving the base end of the spindle, the base journal bearing having a cylindrical inner side wall and an inner end surface; and
   wherein the inner end surfaces of the inlet journal bearing and the base journal bearing are spaced a distance which is greater than a length of the spindle to define axial clearance between the spindle and the inner end surfaces of the bearings in order to avoid damaging blood cells.

2. The centrifugal pump of claim 1 wherein the coupling means comprises:
   magnetic means carried by the impeller for magnetically coupling with the external source of rotation for rotating the impeller about the spindle axis of rotation.

3. The centrifugal pump of claim 1 wherein the base journal bearing and the inlet journal bearing do not rotate with respect to the housing.

4. The centrifugal pump of claim 1 wherein:
   the inlet is disposed externally of the pumping chamber and includes a tube circumferential wall; and
   the inlet journal bearing is supported from the tube circumferential wall of the inlet.

5. The centrifugal pump of claim 4 wherein:
   the inlet curves so that the tube circumferential wall crosses the spindle axis of rotation.

6. The centrifugal pump of claim 1 and further comprising means for counteracting a tendency of the impeller to move axially toward the inlet when the impeller is rotating.

7. The centrifugal pump of claim 1 wherein the impeller carries blades on a first side facing the inlet and has a plurality of grooves on a second, opposite side.

8. A centrifugal pump for pumping biological fluids such as blood, comprising:
   a housing defining a pumping chamber with an inlet and an outlet;

a spindle enclosed within the pumping chamber and positioned along a spindle axis, the spindle comprising an inlet end toward the inlet of the pumping chamber and a base end opposite the inlet end;

means of rotation disposed externally of the pumping chamber;

an impeller enclosed within the pumping chamber and being supported on the spindle in a spaced relationship to the means of rotation, the impeller comprising coupling means for coupling with the means of rotation for rotating the impeller about the spindle axis;

an inlet journal bearing supported from the housing for rotatably supporting and receiving the inlet end of the spindle, the inlet journal bearing having a cylindrical inner side wall and an inner end surface;

a base journal bearing supported from the housing for rotatably supporting and receiving the base end of the spindle, the base journal bearing, having a cylindrical inner side wall and an inner end surface; and wherein the inner end surfaces of the inlet journal bearing and the base journal bearing are spaced a distance which is greater than a length of the spindle to define axial clearance between the spindle and the inner end surfaces of the bearings in order to avoid damaging blood cells.

9. The centrifugal pump of claim 8 wherein the impeller carries blades on a first side facing the inlet and has a plurality of grooves on a second, opposite side.

10. A centrifugal pump for pumping biological fluids such as blood, adapted to be coupled with an external source of rotation, comprising:

a housing defining a pumping chamber with an inlet and an outlet;

a spindle enclosed within the pumping chamber for rotation about a spindle axis, the spindle comprising an inlet end and a base end opposite the inlet end;

an impeller enclosed within the pumping chamber and being supported on the spindle in a spaced relationship to the external source of rotation, the impeller comprising coupling means for coupling with the external source of rotation for rotating the impeller about the spindle axis of rotation;

an inlet journal bearing embedded in an inlet wall of the pumping chamber for rotatably supporting and receiving the inlet end of the spindle, the inlet journal bearing having a cylindrical inner side wall and an inner end surface;

a base journal bearing supported from the housing for rotatably supporting and receiving the base end of the spindle, the base journal bearing having a cylindrical inner side wall and an inner end surface; and wherein the inner end surfaces of the inlet journal bearing and the base journal bearing are spaced a distance which is greater than a length of the spindle to define axial clearance between the spindle and the inner end surfaces of the bearings in order to avoid damaging blood cells.

11. The centrifugal pump of claim 10 further comprising a base journal bearing for rotatably supporting and receiving the base end of the spindle.

12. A centrifugal pump for pumping biological fluids such as blood, comprising:

a housing defining a pumping chamber with an inlet and an outlet;

a spindle enclosed within the pumping chamber and positioned along a spindle axis, the spindle comprising an inlet end inserted in a first journal bearing, the first journal bearing having a cylindrical inner side wall and an inner end surface and a base end inserted in a second journal bearing opposite the inlet end, the second journal bearing having a cylindrical inner side wall and an inner end surface, wherein the first journal bearing is embedded in an inlet wall of the pumping chamber and the inner end surfaces are spaced a distance which is greater than a length of the spindle to define axial clearance between the spindle and the inner end surfaces of the bearings in order to avoid damaging blood cells;

means of rotation disposed externally of the pumping chamber; and an impeller enclosed within the pumping chamber and being supported on the spindle in a spaced relationship to the means of rotation, the impeller comprising coupling means for coupling with the means of rotation for rotating the impeller about the spindle axis.

* * * * *

UNITED STATES PATENT AND TRADEMARK OFFICE
CERTIFICATE OF CORRECTION

PATENT NO. : 5,360,317

DATED : November 1, 1994

INVENTOR(S) : EARL W. CLAUSEN, LLOYD C. HUBBARD

It is certified that error appears in the above-indentified patent and that said Letters Patent is hereby corrected as shown below:

Col. 5, line 36, delete "of is spindle 16", insert --of spindle 16 is--

Signed and Sealed this

Twenty-fifth Day of April, 1995

Attest:

BRUCE LEHMAN

Attesting Officer

Commissioner of Patents and Trademarks